United States Patent [19]

Schwuchow

[11] Patent Number: 5,691,816
[45] Date of Patent: Nov. 25, 1997

[54] COMPACT DENSITOMETER DEVICE

[76] Inventor: Klaus Schwuchow, Walter Kollow Strasse 39, 65812 Bad Soden/Taunus, Germany

[21] Appl. No.: 606,658

[22] Filed: Feb. 26, 1996

Related U.S. Application Data

[63] Continuation of Ser. No. 220,589, Mar. 31, 1994, abandoned.

[30] Foreign Application Priority Data

Mar. 31, 1993 [DE] Germany .................. 9304880 U

[51] Int. Cl.$^6$ .................................................. G01J 3/46
[52] U.S. Cl. ......................................................... 356/402
[58] Field of Search .......................... 356/402–411, 443

[56] References Cited

U.S. PATENT DOCUMENTS 4,518,234  5/1985  Lamefe ........................ 356/443 X
4,907,036  3/1990  Morita ............................ 356/404
5,051,654  9/1991  Nativi et al. .................... 356/506
5,063,583  11/1991  Galkin ............................ 378/207
5,141,323  8/1992  Kipphan et al. ............... 356/406

FOREIGN PATENT DOCUMENTS 364 18 46 A1  6/1988  Germany .

Primary Examiner—K. Hantis
Attorney, Agent, or Firm—Fulbright & Jaworski LLP

[57] ABSTRACT

The invention relates to a device for universal quality inspection of material to be exposed, especially of technical films and x-ray films, using an exposure means designed as a sensitometer, and a densitometer, which are combined into a single device. A densitometer is combined with a light source for individual measurements for determining the behavior of the density curve of a film with a densitometer designed as a measurement arm. A luminescent film which can be excited in two colors and which lies in one plane is used as a light source for the sensitometer.

19 Claims, 3 Drawing Sheets

COMPACT DENSITOMETER DEVICE

This is a continuation application of application Ser. No. 08/220,589, filed Mar. 31, 1994 abandoned.

I. BACKGROUND OF THE INVENTION

A. Field of the Invention

The invention relates to a device for universal quality inspection of material to be exposed, especially of technical films and x-ray films, using an exposure means designed as a sensitometer, and a densitometer.

B. Description of the Related Technology

Numerous methods and devices are already known for measuring the color density or density steps of film. To determine the density steps or the gradation of the black-and-white film, it has been necessary in the past to produce a so-called gray wedge from the film to be measured. A gray wedge represents a light filter of gray color with continuously or gradually rising absorption.

Gradation of a film is defined as the relation between the exposure and optical transmission density which can be produced in the photographic layer. Since the sensitivity of the eye changes logarithmically, a gray wedge to be produced must be constructed with logarithmic behavior of the optical transmission density. However, linear measurement methods are also used.

Characteristics values which are sufficiently meaningful for quality, usefulness and applicability can be determined from the gradation curve or the characteristic curve of a film. Among other things, the gradation of a film and thus its characteristic values are subject to changing due to aging and chemical development, which, for its part, depends on the quality of the chemicals used and the number of baths. Appropriate exposure can balance changes of the gradation under certain circumstances. This balancing by intensified exposure is not allowable and is dangerous especially when x-ray films are involved. If an increased dose of radiation is used to balance a faulty film, due to technical defects of the film material, the patient receives an increased radiation burden which can be avoided. For these reasons it is especially important to determine and measure the sensitivity and the gradation of each film by continuous measurements of specific samples. In this regard it is important that these measurements can be taken safely, accurately and quickly even by unskilled individuals.

In methods known to date, a gray wedge produced on a film sample with about 21 levels and a density increase of 0.15 from level to level, is controlled by a device equipped with a photocell, the device displaying the respective measured values. The values must be read off individually by the operator and graphically evaluated. To do this, a gradation curve is plotted from which the characteristic values such as the gray fog, sensitivity, gradation and maximum density are determined. To determine a tolerance band of the various films, these values must be recorded in a table and compared to one another. Typical measurement errors in this known method are inaccurate positioning of the density step to be measured under the photocell, also reading errors and errors in graphic evaluation. These errors not only can add to one another, but also multiply one another, especially with consideration of logarithm quantities.

To solve these problems, it is known from DE-OS 36 41 846 that the characteristic curve or the gradation curve can be automatically recorded and the characteristic values can be automatically computed from measured values and displayed. Measurement and handling errors of the operator are thus almost precluded.

To be able to draw final conclusions about the quality and thus the usefulness of a technical film or x-ray film, however, it is necessary to take a densitometer measurement afterwards.

Therefore, to determine the quality of a film it is therefore necessary to carry out two processes, specifically, irradiation of a gray wedge and subsequent densitometer measurement, for which two separate and different devices are needed. The devices necessary for this purpose are not only sophisticated and thus expensive, but their operation is also complex, especially with consideration of the fact that the irradiation and measurements can or must be carried out in a dark room.

II. SUMMARY OF THE INVENTION

Therefore, the problem addressed by the invention is to provide an inexpensive device with a corresponding circuit, with which quality inspection of a film of the aforementioned type and also individual measurements can be carried out in a simple and safe manner, in which the device should be suited for battery operation and there should be simple adaptation to the spectral sensitivity of the film to be tested.

The solution to this problem according to the invention comprises a device which has the hardware combination and functional combination of a sensitometer equipped with a switchable luminescent film as a light source for irradiating a gray wedge, an automatic densitometer for determining the behavior of the exposure-density relationship of a film, and a densitometer, designed as a measurement arm with a light source for taking the individual measurements.

The automatic densitometer, the measurement arm for individual measurements, and the sensitometer may be located in a housing according to this invention. For this reason, not only is the construction compact, but an entire series of electronic circuits and assemblies can be used jointly so that the cost is greatly reduced.

To refine the measurement system, the densitometer may have an automatic test section which is equipped with a motor drive for transport of the film through the test section. All density values of the gray wedge are recorded via the automatic test section and evaluated conventionally and logarithmically via an EPROM.

The luminescent source may be formed as a foil in the conventional manner and has light emitting layers which emit green and blue and which can be excited by electrical fields which are different in terms of their frequency and voltage level. The light intensity transmitted from the luminescent foil is also dependent on the frequency and the voltage level.

In a development of the invention the light emitting layers of the luminescent foil which emit green and blue are formed as luminescent strips which lie close together in one plane, which are electrically isolated from one another, and which are arranged in alternating sequence with respect to their color emission. Thus the two desired light colors are advantageously generated and transmitted in the same plane.

According to the invention, a diffusing disk may be provided between the luminescent foil and the film to be illuminated for uniform distribution of the light over the entire luminous surface.

In one embodiment of the invention, the light source transfer switch may be coupled to an acoustic signaller. This greatly increases operating safety since the exposure operations take place in a darkened space illuminated only with red light so that misadjustments are prevented with the acoustic signalling.

In another embodiment of the invention, the light source transfer switch may be coupled to a coding device in order to provide the film to be exposed with an identification which corresponds to its color sensitivity. Thus, the film can be clearly identified in a secure manner with respect to its spectral sensitivity. The coding device may be advantageously equipped with light emitting diodes which project a corresponding image on the film to be exposed using a template.

The densitometer designed as a measurement arm with the housing of the hardware combination has, on one end, a device for executing vertical tilting motion of the measurement arm, and, on its other end, it has a light beam receiver connected to an evaluation device, opposite which is a light source which acts in combination with the radiation receiver and which is mounted in the housing of sensitometer. With this device it is possible to measure fields of a film which lie at most the length of the measurement arm away from the edge of the film. The measurement arm has a digital display device for convenient reading of the measured values.

III. BRIEF DESCRIPTION OF THE DRAWINGS

IV. DETAILED DESCRIPTION OF THE PREFERRED EMBODIMENT

Figure 1:
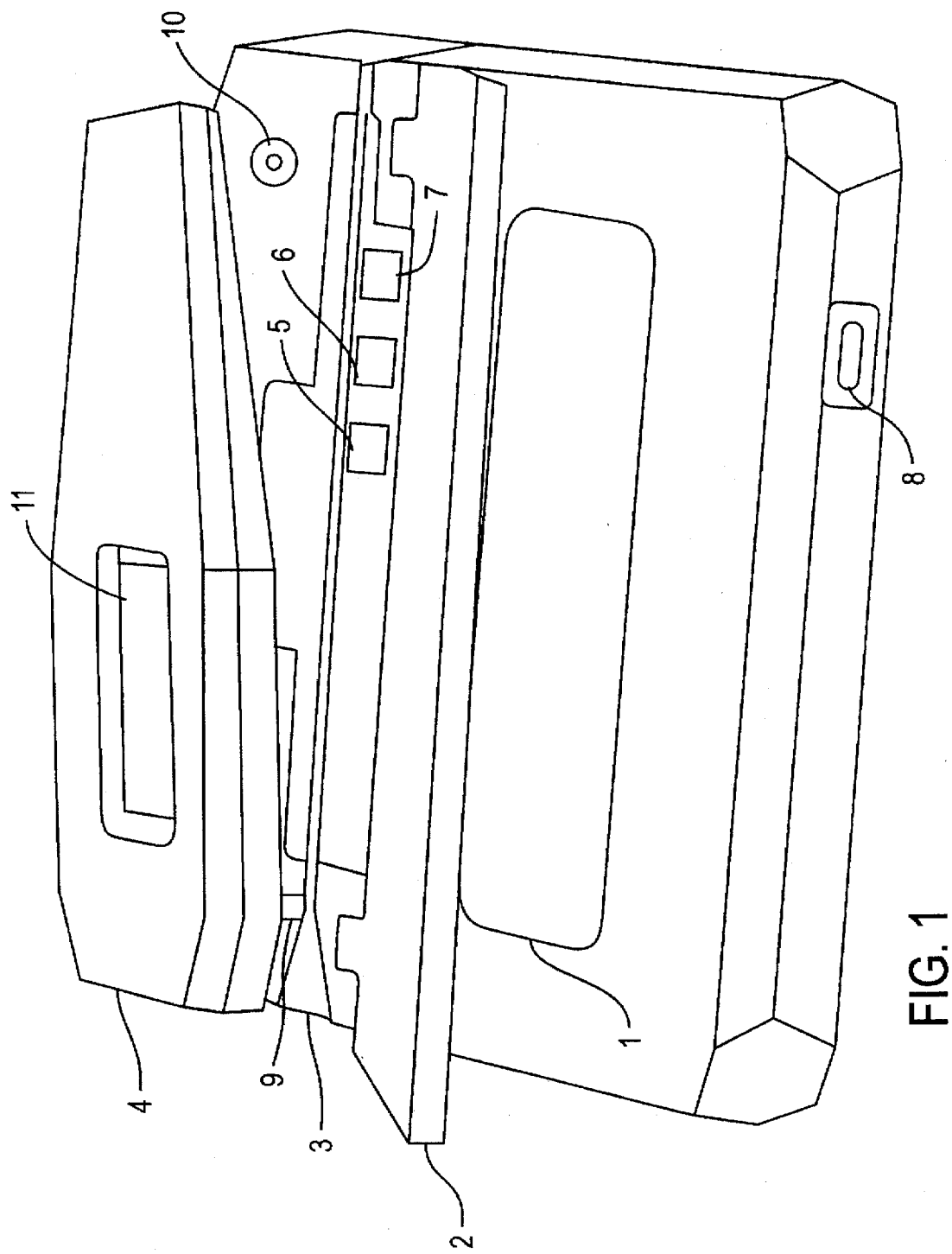
FIG. 1 shows a perspective representation of one embodiment of the invention.

In FIG. 1 the sensitometer housing is labeled 1 with partially opened cover 2. An automatic test section is labeled 3, and, on the rear part of the equipment is removable measurement arm 4, for taking individual measurements, which is mounted to tilt around tilting device 9. Under the front part of tiltable measurement arm 4 is light source 10, in housing 1, which acts in combination with a radiation receiver in the measurement arm. Measurement arm 4 enables measurement of large area films. To do this, the film is pushed between housing 1 and measurement arm 4 and the point to be measured is moved above light source 10. Measurement arm 4 is then tilted down so that between light source 10 and the light beam receiver there is only a minimum distance. The measurement result is immediately digitally reproduced in display 11.

The equipment is operated using switches 5, 6, and 7. Switch 8 enables switching from a green to a blue light source which have corresponding crystals for generating a pure spectral light distribution at the time which will be detailed below.

Figure 2:
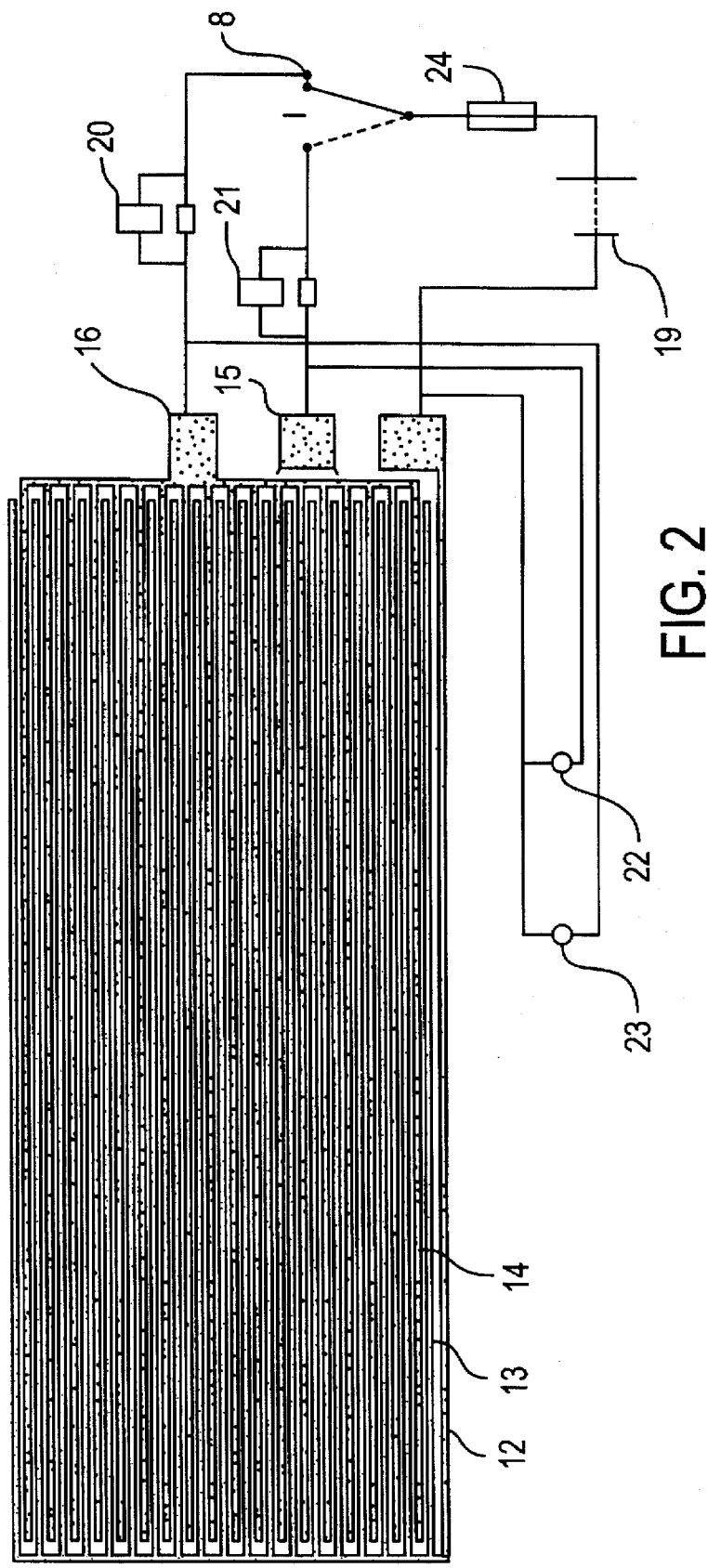
FIG. 2 shows an overhead view of a luminescent foil for two colors, for example, in natural size.

FIG. 2 shows an overhead view of luminescent foil 12 for green and blue light. For this purpose, correspondingly doped crystals are located on extremely small film strips 13 and 14 which are electrically isolated from one another. The electrical connections for exciting the individual films which can be alternatively excited via switch 8 are labeled 15 and 16. Excitation of the different colors of the luminescent crystals and their brightness takes place by selecting a suitable frequency and electrical voltage. The alternating current voltage can vary between 20 and 220 volts AC and the frequency between 50 Hz and 10 kHz. If the power is supplied with direct current voltage source 19, accordingly a DC/AC converter 24 should be provided which is only schematically shown here.

Acoustic signalling via loudspeaker or acoustic generator 20 or 21 in a different tone length or tone sequence takes place simultaneously with switching from one color to another using switch 8.

With excitation of luminescent film 12 by actuation of switch 8, light emitting diode 22 or 23 is excited at the same time and an identification characteristic of the light color used is irradiated onto the film so that its sensitivity is optically recorded.

Figure 3:
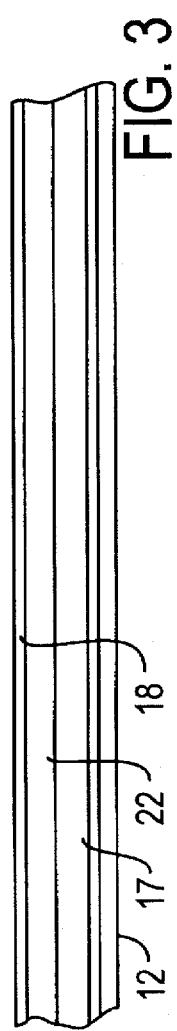
FIG. 3 shows a schematic in a longitudinal section through the structure of the luminescent foil, the scattering surface above it, and the film to be exposed.

FIG. 3 shows a schematic in longitudinal section through the structure of luminescent foil 12, scattering surface 17 above it, cover glass plate 22 and film to be exposed 18.

Figure 4:
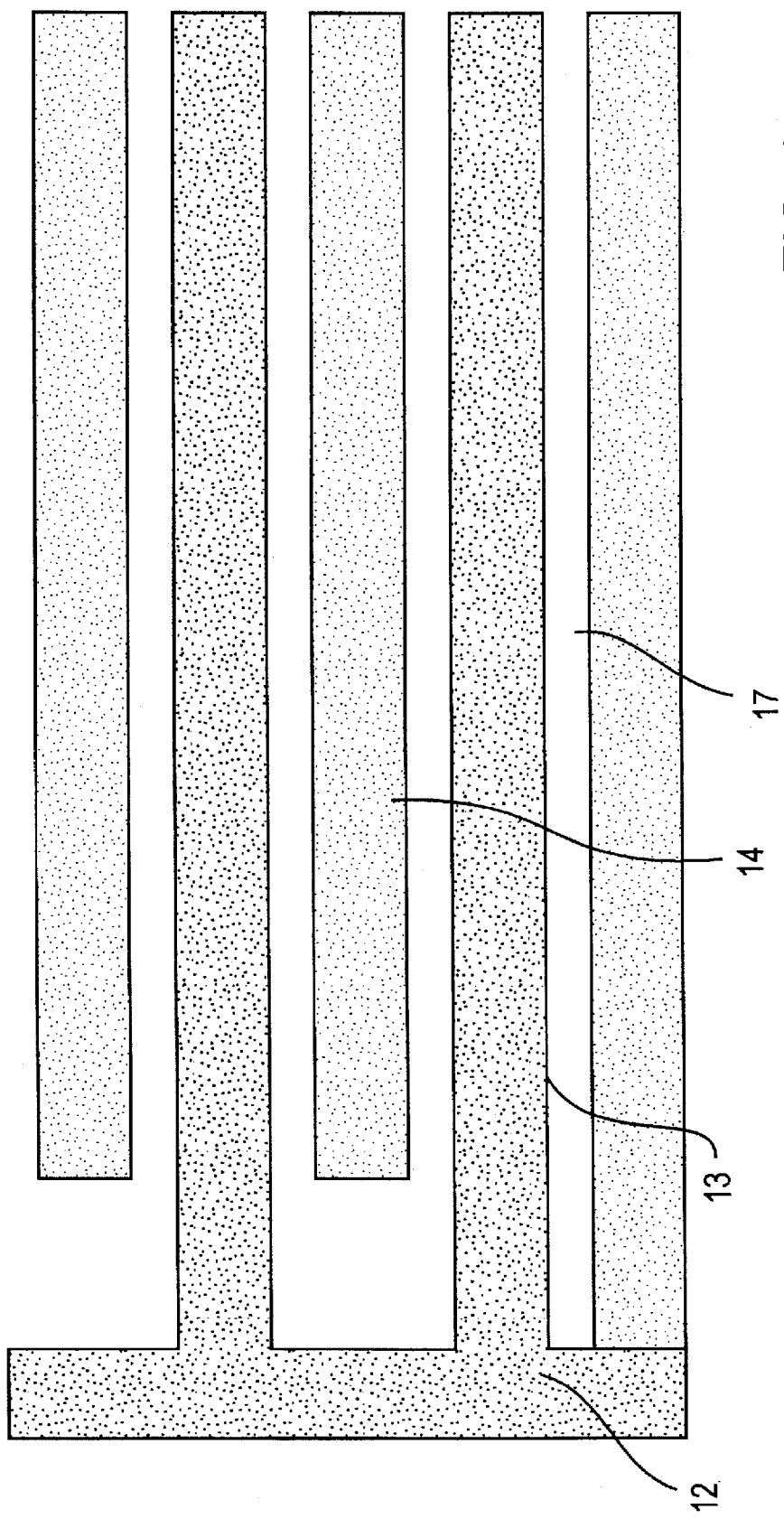
FIG. 4 shows a partial overhead view of the luminescent foil according to FIG. 2, but in a highly enlarged representation.

FIG. 4 shows a partial overhead view of luminescent foil 12 in high enlargement. Film strips 13 and 14 here consist of individual flexible leads which lie close together. Between film strips 13 and 14 are corresponding intervals 17 which are formed as electrical insulation. Film strip 13 when electrically excited emits a monochromatic green light with a wavelength of 510 nm, while film strip 14 when electrically excited emits a monochromatic blue light with a wavelength of 460 nm. Since luminescence is cold light generation, the light is emitted directly with electrical excitation without noticeable time delay and also without persistence effects. This means that the device according to the invention is immediately ready for operation and upon switching from one color emission to another the device is immediately ready for operation in the respective other color as well.

According to the invention, a measurement device is provided with which it is quickly and easily possible to carry out quality inspection of a film, for example x-ray film, regarding the required light color. For this reason only one device with different functions is required; faulty measurements and misexposures are essentially precluded; the device can be easily handled in a dark room, and the selection of the required light which has been turned on is also acoustically signalled. The device according to the invention is a universal, compact sensi-/densitometer for monitoring of film processing and test films with unequalled speed of test results. The device can be operated via power pack or battery. Records, printers or computers which further process, file or transmit the measured values can be connected via the available interfaces.

We claim:

1. A universal film, quality inspection device comprising:
   a housing;
   a sensitometer located within said housing;
   a light source associated with said sensitometer; and
   a densitometer located within said housing, wherein said light source comprises an electrically excitable multicolor luminescent foil.

2. A device according to claim 1, wherein said electrically excitable multicolor luminescent foil is substantially effulgent in one plane.

3. Device according to claim 1, wherein said luminescent foil is comprised of:
   a multiplicity of green light emitting layers responsive to varying electrical fields;
   a multiplicity of blue light emitting layers responsive to varying electrical fields wherein said multiplicity of blue and green light emitting layers of luminescent foil further comprise:

multiple electrically isolated coplanar luminescent strips, sequentially configured with respect to said strips color emission.

4. Device according to claim 1, wherein a uniform light diffusion plate is disposed between said luminescent foil and an exposure film.

5. A device according to claim 1, wherein said densitometer configured as a measurement arm.

6. A universal film quality inspection device according to claim 1, further comprising;

said housing connected to a first end of said measurement arm;

a radiation receiver connected to a second end of said measurement arm;

an evaluation device connected to said second end of said measurement arm wherein said radiation receiver is connected to said evaluation device; and a vertical tilt device connected to said measurement arm.

7. Device according to claim 6, wherein the measurement arm exhibits a digital display device.

8. Device according to claim 6, wherein densitometer exhibits an automatic test section comprised of a film transport motor drive.

9. A universal film quality inspection device according to claim 1, further comprising:

a light source transfer switch connected to said light source and an acoustic signaler responsive to said transfer switch.

10. A universal film quality inspection device according to claim 1, further comprising:

a light source transfer switch connected to said light source and coupled to a color sensitive identification coding device which identifies the color sensitivity exposure.

11. Device according to claim 10, wherein said color sensitive identification coding device exhibits a least one light emitting diode combined with a template.

12. A method for inspecting the quality of unexposed film comprising the steps of:

positioning an unexposed film segment in a sensitometer section of a housing;

electrically exciting a luminescent foil to emit electromagnetic radiations;

exposing said unexposed film segment in the sensitometer section of the housing to predetermined wavelengths of said electromagnetic radiations and measuring the color density or greyness of said exposed film segment in a densitometer section of said housing.

13. A method according to claim 12, wherein said exposing comprises:

exposing said film segment to said radiating light source capable of emitting various predetermined wave lengths of electromagnetic radiation; and uniformly distributing said electromagnetic radiation onto said unexposed film segment.

14. A method according to claim 13, further comprising:

varying the electrical input to said luminescent foil to achieve the emittance of electromagnetic radiation in the green and blue wavelengths.

15. A method according to claim 12, wherein said step for measuring further comprises:

receiving said predetermined wave length of electromagnetic radiation passing through said exposed film segment.

16. A method according to claim 12, wherein said step for measuring further comprises:

measuring responsiveness of said exposed film segment to said predetermined wavelengths of electromagnetic radiation.

17. A method according to claim 12, wherein said step for measuring further comprises:

comparing said responsiveness of said exposed film segment to standardized response tables, characteristic curves, and gradation curves.

18. A method according to claim 12, wherein said step for measuring further comprises:

identifying said exposed film segment according to color sensitivity or grayness.

19. A method according to claim 12, wherein said step for measuring further comprises:

displaying said exposure-density relationship or grayness on a digital display.

* * * * *